United States Patent
Becker et al.

(10) Patent No.: US 9,808,221 B2
(45) Date of Patent: Nov. 7, 2017

(54) ULTRASONIC INTRACAVITY PROBE FOR 3D IMAGING

(75) Inventors: David Becker, Lewistown, PA (US); Terry Wray, McClure, PA (US); Jeffrey Hart, Reedsville, PA (US)

(73) Assignee: Koninklijke Philips N.V., Eindhoven (NL)

( * ) Notice: Subject to any disclaimer, the term of this patent is extended or adjusted under 35 U.S.C. 154(b) by 676 days.

(21) Appl. No.: 10/599,306

(22) PCT Filed: Mar. 22, 2005

(86) PCT No.: PCT/IB2005/050984
§ 371 (c)(1),
(2), (4) Date: Sep. 25, 2006

(87) PCT Pub. No.: WO2005/094689
PCT Pub. Date: Oct. 13, 2005

(65) Prior Publication Data
US 2008/0228081 A1    Sep. 18, 2008

Related U.S. Application Data

(60) Provisional application No. 60/559,321, filed on Apr. 2, 2004.

(51) Int. Cl.
*A61B 8/12* (2006.01)
*A61B 8/00* (2006.01)
*A61B 8/08* (2006.01)

(52) U.S. Cl.
CPC ............. *A61B 8/4461* (2013.01); *A61B 8/12* (2013.01); *A61B 8/483* (2013.01); *A61B 8/4281* (2013.01); *A61B 8/445* (2013.01)

(58) Field of Classification Search
CPC ..... A61B 8/445; A61B 8/4461; A61B 8/4494; A61B 8/12; A61B 8/4281; A61B 8/483
USPC ......................................... 600/459, 462, 463
See application file for complete search history.

(56) References Cited

U.S. PATENT DOCUMENTS

| | | | |
|---|---|---|---|
| 4,007,735 A * | 2/1977 | Magnusson | 601/75 |
| 4,917,096 A * | 4/1990 | Englehart et al. | 600/446 |
| 5,090,414 A | 2/1992 | Takano et al. | |
| 5,178,150 A * | 1/1993 | Silverstein et al. | 600/463 |

(Continued)

FOREIGN PATENT DOCUMENTS

| | | |
|---|---|---|
| DE | 4420221 A1 | 12/1995 |
| JP | 1135335 A | 5/1989 |

(Continued)

*Primary Examiner* — Vani Gupta

(57) ABSTRACT

An intracavity ultrasound probe includes a pivotally mounted array transducer which is oscillated to scan a volumetric region from within the body. The transducer is oscillated by a motor located in the probe handle. The array transducer is immersed in a liquid which acoustically couples ultrasonic energy between the elements of the transducer and the body. The acoustic coupling liquid is located in the distal tip of the probe shaft, where only 6 cc of liquid is required. The small amount of liquid reduces the weight of the shaft of the probe so that the center of gravity of the probe is in the handle, making the probe comfortable and easy to manipulate. The majority of parts in the probe shaft are made of aluminum or other low density materials, keeping the overall weight of the probe to about 250 grams.

19 Claims, 3 Drawing Sheets

(56) References Cited

U.S. PATENT DOCUMENTS

| | | | |
|---|---|---|---|
| 5,722,964 A * | 3/1998 | Herweck | A61M 1/0013 |
| | | | 604/317 |
| 5,740,804 A | 4/1998 | Cerofolini et al. | |
| 5,762,066 A | 6/1998 | Law | |
| 5,799,655 A * | 9/1998 | Jang | A61B 8/12 |
| | | | 600/439 |
| 5,846,205 A * | 12/1998 | Curley et al. | 600/472 |
| 5,882,302 A * | 3/1999 | Driscoll et al. | 600/371 |
| 6,039,694 A * | 3/2000 | Larson et al. | 600/459 |
| 6,315,710 B1 * | 11/2001 | Bushek et al. | 600/25 |
| 6,361,500 B1 * | 3/2002 | Masters | A61B 8/12 |
| | | | 600/466 |
| 6,592,520 B1 | 7/2003 | Peszynski et al. | |
| 6,621,065 B1 * | 9/2003 | Fukumoto et al. | 250/216 |
| 6,784,600 B2 * | 8/2004 | Klee | B06B 1/0688 |
| | | | 252/62.9 R |
| 8,409,102 B2 * | 4/2013 | Griffin | A61B 8/12 |
| | | | 600/407 |

FOREIGN PATENT DOCUMENTS

| | | | |
|---|---|---|---|
| JP | 3289950 A | 12/1991 | |
| JP | 5042151 A | 2/1993 | |
| JP | 2002516586 T | 6/2002 | |
| JP | 200231081 A | 10/2002 | |
| JP | 2003230568 A | 8/2003 | |

* cited by examiner

ULTRASONIC INTRACAVITY PROBE FOR 3D IMAGING

CROSS REFERENCE TO RELATED APPLICATION

This application claims the benefit of U.S. provisional application Ser. No. 60/559,321 filed Apr. 2, 2004, which is incorporated herein.

This invention relates to medical diagnostic imaging systems and, in particular, to intracavity probes for three dimensional imaging for ultrasonic diagnostic imaging systems.

Intracavity ultrasound probes have been in use for many years for imaging the body from within the body. By imaging from within the body internal organs can be imaged more directly without the need to transmit ultrasound waves through intervening tissue and body structure. For example, transesophageal probes can image the heart and abdominal organs from the esophagus or stomach and avoid the need to send and receive ultrasound through or around the ribs. The present invention relates to intracavity probes inserted in the vagina (IVT probes) or rectum (ICT probes) to image the cervix, uterus, or prostate.

In the past, IVT and ICT probes have scanned a two dimensional image region from within the body. This could be done with an array transducer or oscillating single crystal transducer which would scan a sector-shaped area of the body. By curving the elements of an array transducer completely around the distal tip region of the probe, sectors approximating 180° could be scanned. A typical IVT intracavity probe 10 is shown in FIG. 1. This probe includes a shaft portion 12 of about 6.6 inches (16.7 cm) in length and one inch in diameter which is inserted into a body cavity. The ultrasound transducer is located in the distal tip 14 of the shaft. The probe is grasped and manipulated by a handle 16 during use. At the end of the handle is a strain relief 18 for a cable 20 which extend about 3-7 feet and terminates at a connector 22 which couples the probe to an ultrasound system. A typical IVT probe may have a shaft and handle which is 12 inches in length and weigh about 48 ounces (150 grams) including the cable 20 and the connector 22.

In recent years ultrasound systems have been introduced with three dimensional (3D) imaging capability and intracavity probes have been designed to perform 3D imaging. Generally this is done by replacing the array transducer which is statically affixed in the distal tip with an array transducer which can be oscillated rapidly in the elevation direction. This oscillation will sweep the image plane being scanned through a volumetric region, acquiring multiple adjacent planar images which can be rendered into a three dimensional image. However, as was the case with earlier oscillating single crystal or annular array transducers, the oscillating array transducer of the 3D probe must be contained within a fluid through which it can oscillate and which is highly transmissive of ultrasound. Generally this fluid will be a water or oil-based solution such as a mineral oil. The fluid is preferably biocompatible so as not to injure or irritate the tissues of the patient in the event of leakage.

These mechanically oscillating 3D array probes will generally house the motor for the oscillation drive within the handle of the probe, thereby keeping it outside the body of the patient. This motor location then mandates a fluid compartment for the oscillating mechanism and transducer which extends through most of or all of the shaft and distal tip of the probe. The fluid will comprise a large portion of the weight of the probe which is located in the shaft of the probe, causing the center of gravity of the probe to be forward of the handle and in the shaft of the probe. This imbalance makes the intracavity probe unwieldy and difficult to manipulate easily. It would be desirable to reduce the forward weight and balance of the probe so that the 3D intracavity probe is easier to manipulate during a diagnostic procedure.

In accordance with the principles of the present invention a 3D intracavity probe includes an array transducer in the distal tip which is swept to scan a volumetric region. The array transducer is swept by motor which is located in the handle of the probe. The array transducer is contained within a fluid chamber located at the distal tip of the probe and requiring less than 10 cc of fluid. As a result, the center of gravity of the shaft and handle is located in the handle and not the shaft, making the probe easier and more comfortable to hold and manipulate during use.

In accordance with further aspects of the present invention, the array transducer is mounted on an array mount made of a low mass material and displacing space within the chamber which otherwise would be filled with fluid, thereby reducing the fluid volume of the chamber. The shaft and shaft components, except for critical wear surfaces of the array drive mechanism, are also made of low mass materials such as plastics and aluminum. Accordingly, the weight of the probe is less than two-thirds of the weight of prior art 3D intracavity probes.

Figure 1:
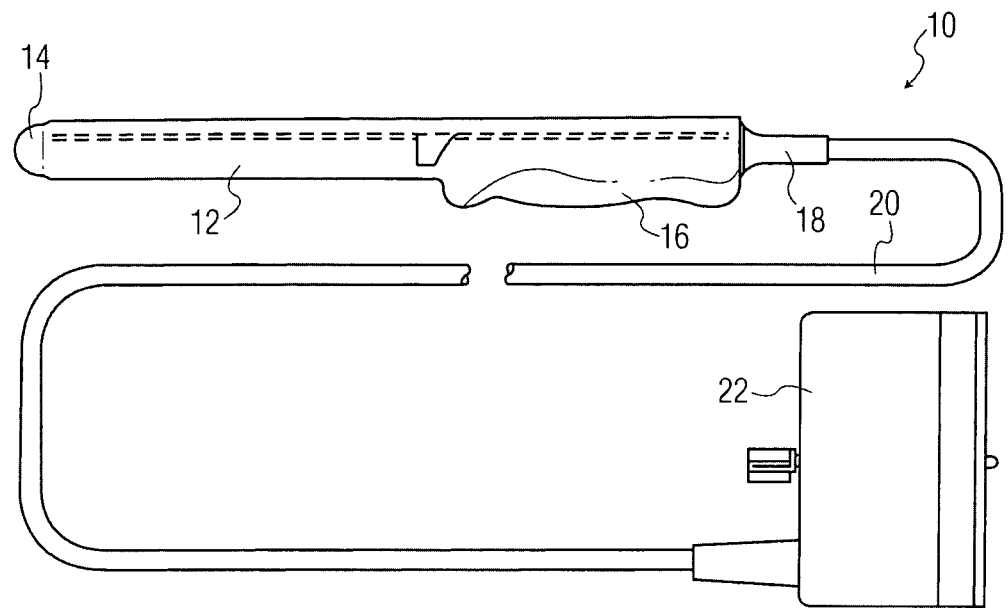
FIG. 1 illustrates a typical intracavity ultrasound probe of the prior art.
Figure 2:
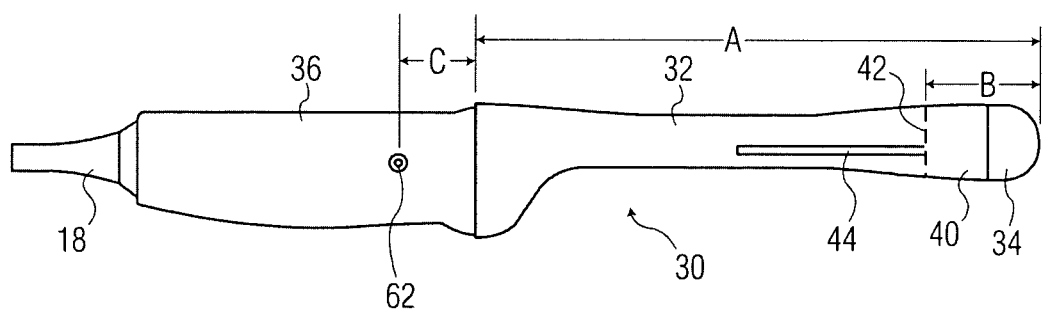
FIG. 2 illustrates a side view of an intracavity probe for three dimensional imaging of the present invention.

Referring now to FIG. 2, an intracavity ultrasound probe 30 of the present invention is shown. The probe 30 includes a handle section 36 by which the user holds the handle for manipulation during use. At the rear of the handle is a strain relief 18 for the probe cable (not shown). Extending from the forward end of the handle 36 is the shaft 32 of the probe which terminates in a dome-shaped acoustic window 34 at the distal end through which ultrasound is transmitted and received during imaging. Contained within the distal end of the shaft is a transducer mount assembly 40 which is also shown in the cross-sectional view of the shaft of FIG. 3 and in the uncovered view of FIG. 4. A convex curved array transducer 46 is attached to a transducer cradle 48 at the distal end of the assembly 40. The transducer cradle 48 is pivotally mounted by its pivot axis 49 to be rocked back and forth in the distal end of the probe and thereby sweep an image plane through a volumetric region in front of the probe. The transducer cradle 48 is rocked by an oscillating drive shaft 50 which extends from a motor and position sensor 60 in the handle 36 to the transducer mount assembly 40. The drive shaft 50 extends through an isolation tube 52 in the shaft which serves to isolate the moving drive shaft from the electrical conductors and volume compensation balloon 44 located in the shaft proximal the transducer mount assembly 40. The drive shaft 50 rocks the cradle by means of two mating bevel gears 54, one at the end of the drive shaft 50 and another on the transducer cradle 48. The motor alternately drives the drive shaft 50 in one direction of rotation and then the other, which alternately rocks the transducer cradle 48 in one direction and then the other, which sweeps the image plane of the transducer array 46 back and forth through the volumetric region in front of the distal end of the probe. The echo signals acquired by the transducer array 46 are beamformed, detected, and rendered by the ultrasound system to form a three dimensional image of the volumetric region scanned by the probe.

Because ultrasonic energy does not efficiently pass through air, the array transducer 46 is surrounded by a liquid which is transmissive of ultrasound and closely matches the acoustic impedance of the body which is approximately that of water. Water-based, oil-based, and synthetic polymeric liquids may be used. In a constructed embodiment silicone oil is used. In accordance with the principles of the present invention, only a small amount of liquid is required in the shaft 32 because the weight of the liquid can contribute significantly to the overall weight of the shaft. In some prior art probes the entire shaft is filled with liquid, adding substantial weight to the shaft and causing the center of gravity of the handle and shaft to be located in the shaft. Other prior art probes have used sizeable elastomeric bags of liquid for the liquid bath of the transducer array. These embodiments also locate the center of gravity of the probe in the shaft, which makes the probe ungainly and difficult to maneuver easily. The liquid used in such embodiments can approach 50 cc, for instance, adding its weight to the probe shaft at the distal end.

In accordance with the principles of the present invention the majority of the liquid bath for the transducer array is contained within the transducer mount assembly 40. The only liquid located to the rear of the back surface 42 of the transducer mount assembly 40 (see FIG. 2) is the small amount of the volume compensation balloon 44. In a constructed embodiment the total amount of liquid in the shaft of the probe is 6.3 cc, of which 95% is contained within the transducer mount assembly 40. Only 0.3 cc of liquid is contained within the volume compensation balloon 44, which can be kept to a small volume of liquid due to the low overall volume of liquid. In the constructed embodiment the length of the shaft 32 was 7.5 inches from the handle to the distal tip (dimension A in FIG. 2). The transducer mount assembly 40 is contained within the distal 1.5 inches of that length (dimension B in FIG. 2). Thus, there is only 6 cc of liquid in the forward half of the probe shaft 32, and only 6.3 cc of liquid in the entire shaft. Ninety-five percent of the liquid is in close proximity to the transducer array, located as it is in the distal 20% of the probe shaft. With so little liquid in the shaft and so little liquid in the forward half of the probe shaft, and the motor located in the handle, the center of gravity 62 of the probe handle and shaft is located in the handle, a full inch behind the handle/shaft interface (dimension C in FIG. 2). With the center of gravity located in the handle the probe is much easier and more comfortable to manipulate during use.

Figure 3:
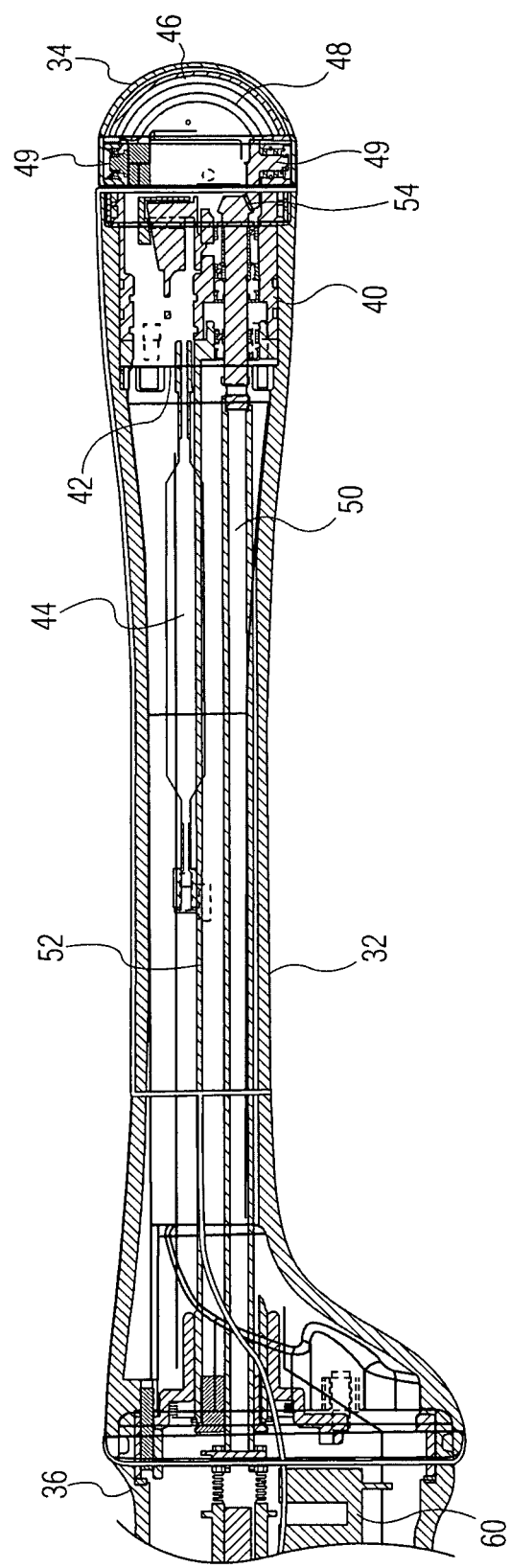
FIG. 3 is a side cross-sectional view of a 3D intracavity probe of the present invention.
Figure 4:
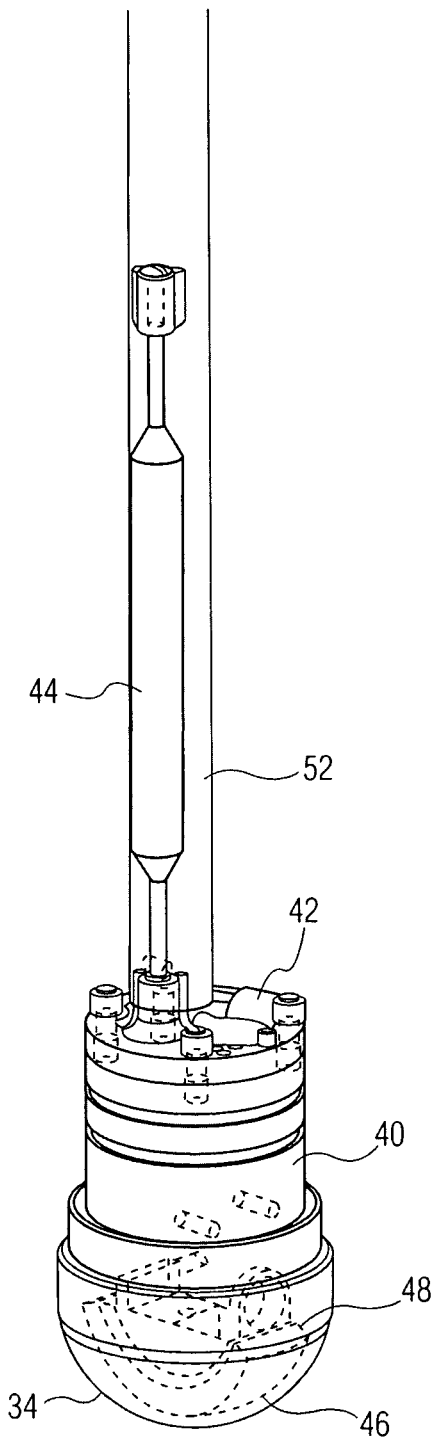
FIG. 4 is a perspective view of the tip assembly of a 3D intracavity probe of the present invention.

In addition to the small amount of fluid needed in the forward section of the shaft, the embodiment of FIGS. 3 and 4 employ additional measures to reduce the amount of liquid and the weight of the probe shaft 32. Only critical wear surfaces within the shaft 32, such as the drive shaft 50, the gears 54, and pivot points for the transducer cradle are made of stainless steel. Selected fasteners and fittings are also made of stainless steel. Other components within the shaft are made of lighter materials with a density lighter than that of stainless steel. The transducer cradle 48 is made of three pieces of aluminum and is tapered on the sides which are the leading edges as the cradle travels through the liquid. The tapering on either side causes the cradle to move more easily through the liquid with less resistance. The space behind the transducer array and backing is not hollow but is filled so as to displace volume that would otherwise be occupied by liquid, further reducing the liquid needed in the distal end of the probe. The main body of the transducer mount assembly 40 is also made of aluminum, as is the isolation tube 52. The volume compensation balloon 44 is made of a thin plastic. The transducer array and its backing are made of material customarily used for those purposes such as piezoelectric ceramic and epoxy. This use of lightweight materials enables a constructed embodiment of the present invention including the probe shaft and handle to weigh only 250 grams, compared to the 400 gram weights of prior art probes.

What is claimed is:

1. An ultrasonic intracavity probe for scanning a volumetric region from within the body comprising:
    a handle section to be held during use of the probe; and
    a shaft section having a distal end which is to be inserted into a body cavity during use of the probe;
    a pivotally mounted convex array transducer enclosed by a rigidly dimensioned compartment of a transducer mount assembly at the distal end of the shaft section and facing a direction in front of the probe, wherein a space behind the convex array transducer in the rigidly dimensioned compartment of the transducer mount assembly is at least partially filled with a backing material;
    a motor located in the handle section;
    a drive shaft coupled to the motor and further coupled to the array transducer via two mating gears having perpendicular input and output axes, wherein the drive shaft is configured to move the convex array transducer during scanning to sweep an image plane through a volumetric region extending in front of the probe, and wherein the motor rotates the drive shaft so as to sweep the image plane; and
    a liquid bath constrained to the shaft section to the exclusion of the handle section and located in the compartment of the transducer mount assembly at the distal end of the shaft section, wherein a majority of the liquid bath is located within the transducer mount assembly and a remaining portion of the bath is contained within a volume compensation balloon extending along the shaft section proximal of the transducer mount assembly, wherein the backing material displaces a volume in the transducer mount assembly that would otherwise be occupied by the liquid bath,
    wherein at least a volume of the liquid bath is selected such that the center of gravity of the probe is located in the handle section.

2. The ultrasonic intracavity probe of claim 1, wherein the transducer mount assembly has a proximal termination within one and one-half inches of the terminus of distal end of the shaft section.

3. The ultrasonic intracavity probe of claim 2, wherein 90% of the liquid bath is contained within the transducer mount assembly.

4. The ultrasonic intracavity probe of claim 1, wherein the liquid bath has a volume of less than 25 cc of liquid.

5. The ultrasonic intracavity probe of claim 4, wherein the liquid bath has a volume of less than 10 cc of liquid.

6. The ultrasonic intracavity probe of claim 5, wherein the liquid bath has a volume of approximately 6 cc of liquid.

7. The ultrasonic intracavity probe of claim 1, wherein 90% of the liquid bath is located in the most distal 25% of the length of the shaft section.

8. The ultrasonic intracavity probe of claim 7, wherein the liquid bath has a volume of less than 10 cc of liquid.

9. The ultrasonic intracavity probe of claim 1, wherein the transducer mount assembly includes a main body formed of a material which is lighter than stainless steel.

10. The ultrasonic intracavity probe of claim 9, wherein the array transducer is pivotally mounted to the transducer mount assembly by a transducer cradle, wherein the transducer cradle is made of a material which is lighter than stainless steel.

11. The ultrasonic intracavity probe of claim 10, wherein the transducer cradle includes a solid body located behind the array transducer which displaces volume in the transducer mount assembly that would otherwise be occupied by the liquid bath.

12. The ultrasonic intracavity probe of claim 10, wherein the transducer cradle is tapered so as to pass more easily through the liquid bath.

13. The ultrasonic intracavity probe of claim 9, wherein the transducer mount assembly includes wear surfaces which are made of stainless steel.

14. The ultrasonic intracavity probe of claim 13, wherein the wear surfaces are part of the drive shaft.

15. The ultrasonic intracavity probe of claim 9, wherein the weight of the probe is less than 400 grams.

16. The ultrasonic intracavity probe of claim 15, wherein the weight of the probe is less than 300 grams.

17. The ultrasonic intracavity probe of claim 16, wherein the weight of the probe is approximately 250 grams.

18. The ultrasonic intracavity probe of claim 16, wherein the drive shaft is the only component made of a material equal to the density of stainless steel or greater.

19. The ultrasonic intracavity probe of claim 1, wherein the mating gears are bevel gears.

* * * * *